United States Patent
Sandeman et al.

(10) Patent No.: US 7,217,831 B2
(45) Date of Patent: May 15, 2007

(54) INSECTICIDE AND METHOD OF CONTROLLING INSECTS

(75) Inventors: Richard Mark Sandeman, Cottles Bridge (AU); David Spencer Chandler, Mickleham (AU); Ann Maree Duncan, Northcote (AU); Phillip Maxwell Hay, Melton (AU)

(73) Assignee: Nufarm - Australia Limited, Victoria (AU)

( * ) Notice: Subject to any disclaimer, the term of this patent is extended or adjusted under 35 U.S.C. 154(b) by 28 days.

(21) Appl. No.: 10/674,196

(22) Filed: Sep. 29, 2003

(65) Prior Publication Data

US 2004/0176424 A1    Sep. 9, 2004

Related U.S. Application Data

(63) Continuation of application No. PCT/AU02/00389, filed on Mar. 28, 2002.

(30) Foreign Application Priority Data

Mar. 29, 2001 (AU) .................................. PR4069

(51) Int. Cl.
  *C07F 9/32* (2006.01)
  *C07F 9/30* (2006.01)
  *C07F 9/28* (2006.01)

(52) U.S. Cl. .................. 558/169; 558/70; 558/117; 558/153; 560/17; 560/16; 560/11; 560/8; 560/10

(58) Field of Classification Search ................ 560/17, 560/16, 11, 8, 10; 558/117, 70, 153, 169
  See application file for complete search history.

(56) References Cited

FOREIGN PATENT DOCUMENTS

| BE | 903416 | 4/1986 |
| ES | 522989 | 7/1985 |
| WO | 01/094358 | 12/2001 |

OTHER PUBLICATIONS

Kanaoka, M. et al. (1979) Synthesis of Bassianolide and Its Two Homologs, Enniatin C and Decabassianolide, Agric. Biol. Chem. vol. 43(5), pp. 1079-108.
Singh, M. et al. (1986) Compatibility of Chlorpyrifos (Lorsban 4E) with several herbicides as tank mix, Proc. Fla. State Hort. Soc., vol. 99, pp. 48-51.
Hedley, M.E. et al. (1979) Screening of Selected Agricultural and Industrial Chemicals as Wood Preservatives, Int. Biodeterior. Bull., vol. 15 (1) pp. 9-18.
Hedin, P.A. et al. (1988) Effects of Bioregulators on Flavenoids, Insect Resistance, and Yield of Seed Cotton, J. Agric. Food Chem., vol. 36, pp. 1055-1061.
Hedin, P.A. et al. (1988) Effects of Plant Bioregulators on Nutrients, Insect Resistance and Yield of Corn (Zea mays L.), J. Agric. Food chem., vol. 36, pp. 746-748.
Quimby, P.C. and Frick, K.E. (1985) Evaluation of Herbicide-Coated Larvae of *Bactra verutana* [Lep.: Torticidae] to control Nutsedges [*Cyperus rotundus* L. and *C. esculentus* L.], Entomophaga, vol. 30(3), pp. 287-292.
Yokoyama, V.Y. and Pritchard, J. (1984) Effect of pesticides on Mortality, Fecundity, and Egg Viability of *Geocoris pallens* (Hemiptera: Lygaeidae), J. Econ. Entomol., vol. 77(4), pp. 876-879.
Whitehouse, D.M. and Brown, V.K. (1993) Herbicides in Farm Foresty: Effects on Non-Target Insects, Brighton Crop Protection Conference—Weeds, vol. 1, pp. 121-126.
Mascarenhas, V.J. and Griffin, J.L. (1997) Weed control interactions associated with Roundup and insecticide mixtures, Proc. Beltwide Cotton Conf., vol. 1, pp. 799-801.
Pankey, J.H. et al. (1999) Early season pest management in cotton with Roundup Ultra-insecticide combinations, Proc.- Beltwide Cotton Conf., vol. 2, pp. 981-983.
Spengler, J. et al. (2001) Asymmetric Pictet-Spengler reactions: synthesis of 1, 2, 3, 4-tetrahydroisoquinoline carboxylic acid (Tic) chimeras, Synthesis 2001, No. 10, pp. 1513-1518.

(Continued)

*Primary Examiner*—Elvis O. Price
(74) *Attorney, Agent, or Firm*—Synnestvedt & Lechner LLP

(57) ABSTRACT

An insecticide of formula 1

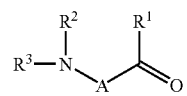

and the agriculturally acceptable salts thereof,
wherein:
$R^1$ is selected from the group consisting of:
the group $OR^5$ wherein $R^5$ is selected from the group consisting of hydrogen, alkyl, substituted alkyl, aryl, substituted aryl, cycloalkyl, substituted cycloalkyl, heterocyclic and substituted heterocyclic;
the group —$NR_6OH$ wherein $R^6$ is selected from the group consisting of hydrogen, alkyl, substituted alkyl, aryl, substituted aryl, carbocyclic and substituted carbocyclic;
the group $NR^7R^8$ wherein $R^7$ and $R^8$ are independently selected from the group consisting of hydrogen, alkyl, substituted alkyl, aryl, substituted aryl and carbocyclic; and
the group wherein $R^1$ is linked to $R^2$ to form a diradical bridging group;
$R^2$ and $R^3$ are independently selected from the group consisting of hydrogen, alkyl, substituted alkyl, carbocyclic, substituted carbocyclic, aryl, substituted aryl, acyl and substituted acyl; and
A is a diradical linking group which has a molecular weight of preferably less than 200 and more preferably less than 100.

28 Claims, No Drawings

OTHER PUBLICATIONS

Ebata, M. et al. (1966) Analysis of N-methylamino acids by automatic amino acid analyzer and gas-liquid chromatography, J. Chromatog., vol. 25, pp. 1-10.

Wieczorek, P., et al: "Plant-growth-regulating N-(phosphonoacetyl)amines" Pest Management Science, Elsevier, Barking, GB, vol. 40, No. 1, Jan. 1994, ISSN: 1526-498X Compounds 5a, 5b and 5c on p. 58 et 59.

Database CA Online!, Chemical Abstracts Service, Columbus, Ohio, US; Nachev, I.: "N.alpha.,N.omega,-dishosphono-, diphosphinomethyl-L-.alpha.,.omega.-diaminocarboxylic acids" retrieved from STN Database accession No. 110:154839 XP002275998, Compounds with RN 119834-46-7, 119834-58-1 *abstract* & Phosphorus and Sulfur and the Related Elements (1988), 37(3-4), 143-8.

Bakuniak E et al: "Further Studies on Biological Activity of Aminophosphonates Structurally Related to N-(Phophonomethyl) Glycine", Journal of Environmental Sciences and Health B: Pesticides, XX, XX, vol. B18, No. 485, 1983, pp. 485-496, XP000575084; ISSN: 0360-1234; *p. 1, last paragraph* *examples IP04527,4540,4949,4950,4951,4952,5056; table 2.

Database CA Online! Chemical Abstracts Service, Columbus, Ohio, US; Soroka, Miroslaw et al: "N-(.alpha.-Phosphonoalkyl)-.alpha.-aminoa lkanoic acids" retrieved from SIN, Database accession No. 98:16850 XP002275999, RN 84044-03-1 *abstract* & PL 113 889 B (Politechnika Wroclawska, Pol.) Jan. 31, 1981.

INSECTICIDE AND METHOD OF CONTROLLING INSECTS

CROSS-REFERENCE TO RELATED APPLICATIONS

This is a continuation of International Application PCT/AU02/00389, which has an international filing date of Mar. 28, 2002, now pending, which is based on and claims priority to Australian Application No. PR4609, filed Mar. 29, 2001. The aforementioned PCT and Australian applications are hereby incorporated by reference.

The invention relates to insecticidal compounds and compositions for controlling insecticides and to a method of controlling insects using the insecticidal compounds and compositions.

Insecticides are chemicals that are used to control damage or annoyance from insects. Control of insects may be achieved by oral ingestion of stomach poisons, contact poisons that penetrate the cuticle or fumigants that penetrate the respiratory system.

The wide use of insecticides particularly in crop protection has lead to the emergence of resistant insects. There is a need for new types of insecticides which are safe to use.

The invention provides an insecticidal compound of Formula I

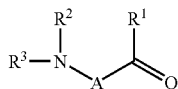

and the agriculturally acceptable salts thereof, wherein:

$R^1$ is selected from the group consisting of:

the group $OR^5$ wherein $R^5$ is selected from the group consisting of hydrogen, alkyl, substituted alkyl, aryl, substituted aryl, cycloalkyl, substituted cycloalkyl, heterocyclic and substituted heterocyclic;

the group —$NR_6OH$ wherein $R^6$ is selected from the group consisting of hydrogen, alkyl, substituted alkyl, aryl, substituted aryl, carbocyclic and substituted carbocyclic;

the group $NR^7R^8$ wherein $R^7$ and $R^8$ are independently selected from the group consisting of hydrogen, alkyl, substituted alkyl, aryl, substituted aryl and carbocyclic; and the group wherein $R^1$ is linked to $R^2$ to form a diradical bridging group;

$R^2$ and $R^3$ are independently selected from the group consisting of hydrogen, alkyl, substituted alkyl, carbocyclic, substituted carbocyclic, aryl, substituted aryl, acyl and substituted acyl; and A is a diradical linking group which has a molecular weight of preferably less than 200 and more preferably less than 100.

The compounds include the agriculturally acceptable salts of compounds of formula I such as the salts formed at the amine moiety, phosphonic acid moiety carboxylic acid moiety and mixtures thereof.

A is preferably a diradical group of formula

wherein the groups $R^{10}$, X and Y are independently selected from the group consisting of hydrogen, alkyl, thiol, hydroxy, thioalkyl, alkoxy, substituted alkyl, carbocyclic, substituted carboxyclic, heterocyclic and substituted heterocyclic; and more preferably $R^{10}$ is hydrogen and X and Y are independently selected from the group consisting of hydrogen, $C_1$ to $C_6$ alkyl, thiol, hydroxy, $C_1$ to $C_6$ thioalkyl, aryl, substituted aryl, $C_1$ to $C_6$ alkoxy, substituted $C_1$ to $C_6$ alkyl, $C_4$ to $C_6$ carboxylic substituted $C_4$ to $C_6$ heterocyclic and substituted $C_4$ to $C_6$ heterocyclic;

p and q are selected from zero, 1, 2 and 3.

The divalent group "A" may be a group wherein the formula

is a naturally occurring amino acid such as alanine, valine leucine, isoleucine, phenylalanine, tyrosine, tryptophan, serine, threonine, methionine, cysteine, pyrroline, hydroxy pyrroline, lysine and histidine.

Preferred A is selected from the group wherein $R^{10}$ is hydrogen, p and q are zero and X and Y are as defined above.

In more the preferred A group X is selected from the group consisting of hydrogen and $C_1$ to $C_6$ alkyl and Y is selected from the group consisting of hydrogen, $C_1$ to $C_6$ alkyl and phenyl.

It is preferred that the substituent $R^1$ is selected from the group consisting of the group $OR^5$ wherein $R^5$ is selected from the group consisting of hydrogen, alkyl, haloalkyl, aryl substituted alkyl, heterocyclic, heterocyclic substituted with alkyl wherein the alkyl is optionally further substituted with hydrocarbyloxy such as $C_1$ to $C_4$ alkoxy;

the group $NR_6OH$ wherein $R^6$ is selected from the group consisting of hydrogen, alkyl, substituted alkyl, aryl, substituted aryl, carbocyclic and substituted carbocyclic;

the group $NR^7R^8$ wherein $R^7$ and $R^8$ are independently selected from hydrogen and $C_1$ to $C_6$alkyl; and the group wherein $R^1$ is linked to $R^2$ to form a bridging group —$R^2$—$R^1$— of formula

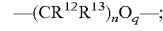

wherein n is 1 or 2, q is zero or 1 and $R^{12}$ and $R^{13}$ are independently selected from hydrogen, halogen, alkyl and haloalkyl.

More preferred $R^1$ is selected from the group consisting of the group $OR^5$ wherein $R^5$ is selected from the group consisting of hydrogen, alkyl, haloalkyl, aralkyl and alkylaryl and wherein more preferred $R^5$ is hydrogen, $C_1$ to $C_6$ alkyl, halogenated $C_1$ to $C_4$ alkyl;

the group $NR^6OH$ wherein $R^6$ is selected from hydrogen and alkyl, preferably from hydrogen and $C_1$ to $C_4$ alkyl and most preferably hydrogen;

the group $NR^7R^8$ wherein $R^7$ and $R^8$ are independently selected from hydrogen and $C_1$ to $C_4$ alkyl.

The preferred group $R^2$ is selected from the group consisting of hydrogen, alkyl, haloalkyl, aryl, alkylaryl and aralkyl;

the group substituted alkyl, substituted haloalkyl, substituted acyl, substituted aryl, substituted alkylaryl and substituted arylalkyl, wherein the subsitutuent is a group of formula

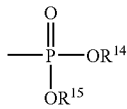

wherein $R^{14}$ and $R^{15}$ are independently selected from the group consisting of hydrogen, halo, alkyl, aryl, alkanoyl, aralkyl, haloalkyl, haloaryl, haloalkyl aryl and haloarylalkyl; and the group wherein $R^2$ is linked to $R^1$ to provide the group —$R^2$—$R^1$— of formula —$(CR^{12}R^{13})_nO_p$— wherein n is 1 or 2, p is 0 or 1 and $R^{12}$ and $R^{13}$ are independently selected from hydrogen, alkyl and haloalkyl.

More preferably $R^2$ is selected from the group consisting of hydrogen $C_1$ to $C_8$ alkyl halo —$(C_1$ to $C_6)$ alkyl and $C_1$ to $C_6$ alkyl substituted by the group of formula

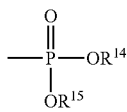

wherein $R^{14}$ and $R^{15}$ are independently selected from the group consisting of hydrogen and $C_1$ to $C_4$ alkyl; and and the group wherein $R^2$ is linked to $R^1$ to provide the group —$R^1$—$R^2$— of formula

—$(CR^{12}R^{13})O$— where $R^{12}$ and $R^{13}$ are independently selected from hydrogen, $C_1$ to $C_4$ alkyl and $C_1$ to $C_4$ haloalkyl.

Even more preferred $R^2$ is selected from the group consisting of hydrogen; and $C_1$ to $C_4$ alkyl; the group of formula

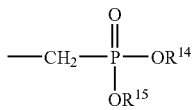

wherein $R^{14}$ and $R^{15}$ are independently selected from the group consisting of hydrogen and $C_1$ to $C_4$ alkyl; and the group wherein $R^2$ is linked to $R^1$ to provide the group —$R^2$—$R^1$— of formula

—$(CR^{12}R^{13})O$— wherein $R^{12}$ and $R^{13}$ are selected from methyl and trifluoromethyl.

Preferably the substituent $R^3$ is selected from the group consisting of hydrogen, alkyl; haloalkyl; aryl; acyl; alkoxycarbonyl-substituted acyl; alkylaryl; aralkyl; and the groups substituted alkyl, substituted haloalkyl, substituted acyl, substituted alkaryl and substituted aralkyl wherein the substituent is the group of formula

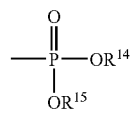

wherein $R^{14}$ and $R^{15}$ are independently selected from the group consisting of hydrogen, alkyl, aryl, aralkyl, alkylaryl, haloalkyl, haloaryl haloalkylaryl and haloaralkyl.

More preferably the substituent $R^3$ is selected from the group consisting of hydrogen, $C_1$ to $C_6$ alkyl, $C_1$ to $C_6$ alkanoyl, $C_1$ to $C_6$ haloalkyl and $C_1$ to $C_6$ alkyl and $C_1$ to $C_6$ alkyl substituted by the group of formula

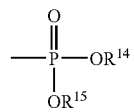

wherein $R^{14}$ and $R^{15}$ are independently selected from the group consisting of hydrogen and $C_1$ to $C_4$ alkyl.

Even more preferably the substituent $R^3$ is selected from the group consisting of hydrogen, $C_1$ to $C_6$ alkyl, $C_1$ to $C_6$ haloalkyl, $C_1$ to $C_4$ alkanoyl and the group of formula

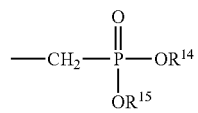

wherein $R^{14}$ and $R^{15}$ are selected from the groups consisting of hydrogen and $C_1$ to $C_4$ alkyl.

In a particularly preferred embodiment the compounds of the invention are of formula Ia

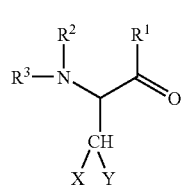

Ia wherein $R^1$, $R^2$ and $R^3$ are as hereinbefore defined and X and Y are independently selected from the group consisting of hydrogen, thiol, alkyl, haloalkyl, aryl, acyl, aralkyl, heterocyclic and heterocyclic alkyl.

The preferred groups X and Y are independently selected from hydrogen, $C_1$ to $C_4$ alkyl, aryl, arylalkyl and heterocyclic.

We have found that compounds of formula Ia are particularly insecticidally active where at least one of $R^2$ and $R^3$ is a group of formula

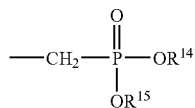

wherein $R^{14}$ and $R^{15}$ are as hereinbefore defined.

Specific examples of such compounds include compounds of formula III

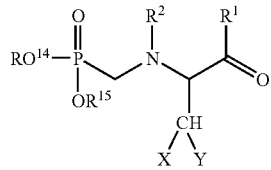

In one embodiment of the compounds of formula I the groups $R^1$ and $R^2$ are linked together to form a diradical linking group —$R^2$—$R^1$—. Such compound preferably have the formula IV and preferred examples of such compounds are of formula IVa

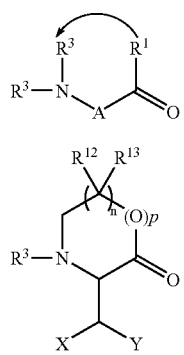

hereinbefore defined.

When groups in formula I such as X and Y include heterocyclic; examples of heterocyclic include 5 and 6 membered rings containing one or two heteroatoms selected from nitrogen, sulphur oxygen wherein the heteroring is optionally fused with a benzene ring. Specific examples include triazenyl, thiazolyl pyrrolyl imidazolyl, pyrazolyl, indolyl, iosoindolyl, indazolyl, indolinyl, isoindolinyl, piperidinyl, piperazenyl, pyridyl, pyrazinyl.

More preferred heterocyclic are indolyl and imidazolyl, most preferably 3-indolyl and 1-H-imidazol-4-yl.

When groups in formula I are, or include alkyl the preferred alkyl is of 1 to 6 carbon atoms and more preferably 1 to 4 carbon atoms.

When groups in formula 1 such as $R^1$, $R^2$, $R^3$, $R^5$, X and Y are substituted groups, such as substituted alkyl, preferred substituents include hydroxy, amino, thio, $C_1$ to $C_4$ alkoxy, $C_1$ to $C_4$ alkylamino, aryl, hydroxyphenyl, halo, haloalkoxy and 5 and 6 membered heterocyclic rings containing one or two heterocarbons wherein the hetero ring is optionally fused with benzene.

When groups in formula I are or include aryl preferred aryl is phenyl.

When groups in formula I are or include acyl preferred acyl is selected from $C_1$ to $C_6$ alkyl carbonyl and benzoyl.

The group HC(X)(Y) in the preferred embodiment is derived from naturally occurring amino acids and accordingly is selected from the group consisting of —$CH_3$, —$CH(CH_3)_2$, —$CH_2CH_2SCH_3$, —$CH_2CH(CH_3)_2$, —$CH_2CH_2CH_2NHCNNH_2$, —$CH_2C_6H_5OH$, —$CH(CH_3)CH_2CH_3$,

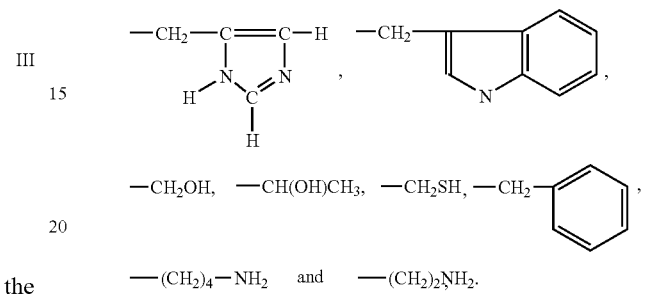

—$CH_2OH$, —$CH(OH)CH_3$, —$CH_2SH$, —$CH_2$—⌬,

—$(CH_2)_4$—$NH_2$ and —$(CH_2)_2NH_2$.

Specific examples of the compounds of formula Ia are shown in Table 1 below:

TABLE 1

Ia

| | $R^1$ | $R^2$ | $R^3$ | X, Y |
|---|---|---|---|---|
| 1. | OH | H | $CH2PO(OH)_2$ | $CH_3$, $CH_3$ |
| 2. | NHOH | H | $CH_2PO(OH)(OCH_3)$ | $CH(CH_3)_2$, H |
| 3. | NHOH | H | $CH_2PO(OH)(OCH_3)$ | $C_6H_5$, H |
| 4. | OH | H | $CH_3$ | H, H |
| 5. | OH | H | $CH_2PO(OH)_2$ | $C_6H_5$, H |
| 6. | NHOH | H | $CH_3$ | H, H |
| 7. | NHOH | H | $CH_2PO(OH)(OCH_3)$ | H, H |
| 8. | —OC($CF_3$)$_2$— | | $CH_2PO(OCH_3)_2$ | —$CH(CH_3)_2$, H |
| 9. | NHOH | H | $CH_3CO$— | $CH_3$, OH |
| 10. | $OCH_3$ | H | $CH_2PO(OCH_3)_2$ | $C_6H_5$, H |
| 11. | —OC($CF_3$)$_2$— | | $BrCH_2$— | $C_6H_5$, H |
| 12. | $OCH_3$ | $CH_2PO(OCH_3)_2$ | $CH_2PO(OCH_3)_2$ | $CH_3$, $CH_3$ |
| 13. | —OC($CF_3$)$_2$— | | $CH_3$ | $C_6H_5$, H |
| 14. | NHOH | H | $CH_2PO(OH)_2$ | $CH_3$, $CH_3$ |
| 15. | OH | H | $CH_3$ | $CH_3$, $CH_2CH_3$ |
| 16. | NHOH | H | $CH_2PO(OH)_2$ | H, $CH(CH_3)_2$ |
| 17. | * | H | H | $CH_3$, $CH_3$ |
| 18. | OH | H | $CH_2PO(OCH_3)_2$ | $CH_3SCH_2$, H |

* = 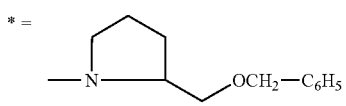

The insecticidal compounds of the invention may be prepared by a range of methods. In a preferred aspect the compounds of formula I and having specific formula ivb, ivc, ivd or ib are prepared according to scheme 1 below:

Scheme 1

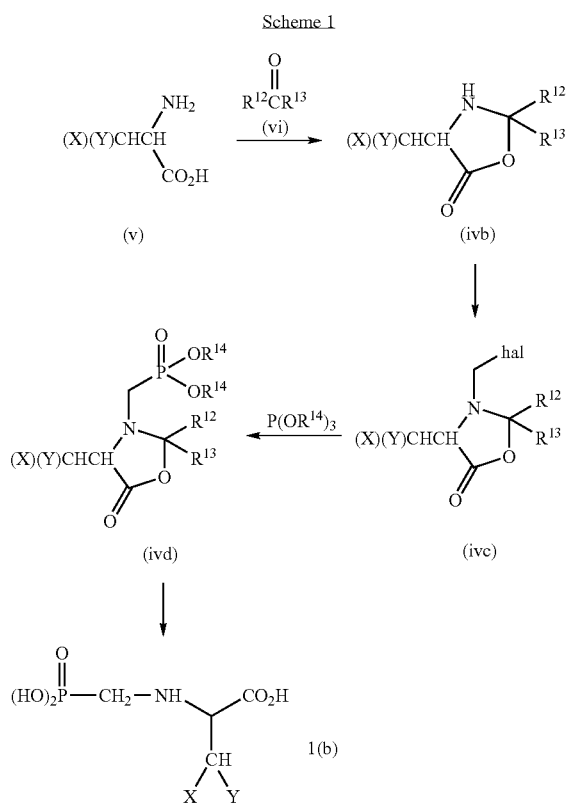

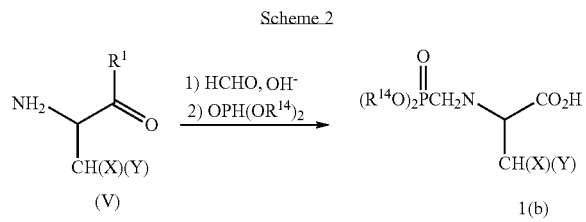

Further compounds of formula 1 may be prepared from the compounds of formula (ivb), (ivc), (ivd) and 1 (b) by suitable methods.

In one aspect the preferred compounds are prepared by reaction of an amino acid of formula (v) with a ketone of formula (vi) to provide a compound of formula (ivb); reaction of the compound of formula (ivb) with paraformaldehyde in the presence of a halogen particularly bromine to provide a compound of formula (ivc) wherein hal is halogen (preferably bromine); reacting the compound of formula (ivc) with a phosphite to provide a phosphonate ester of formula (ivd) and hydrolysis, preferably in aqueous acid, to provide the compound of formula 1(b).

In an alternative method the compounds of the invention are prepared by Mannich reaction as shown in Scheme 2:

Scheme 2

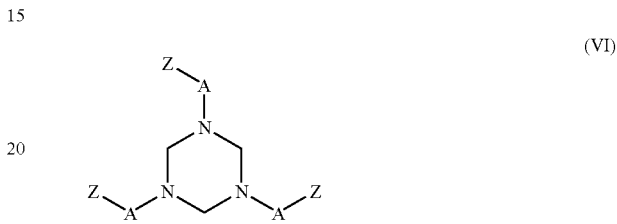

In this method an amino acid (formula V) is reacted with formaldehyde generally in an aqueous metal hydroxide medium. The reaction is preferably carried out with the reactants in approximately equimolar quantities and temperatures in the range of from −5° C. to 15° C. are preferred.

Phosphonomethylation is carried out by addition to the reacting mixture of a lower alkyl phosphite preferably dimethyl phosphite or diethyl phosphite. The phosphite is preferably approximately equimolar with respect to the amino acid. The reaction may be heated to a temperature in the range of from 50° C. to 100° C. to form the N-phosphonomethylated amino acid as the (formula 1b where $R^{14}$ is lower alkyl) diethyl or monoethyl ester. The ester may optionally be hydrolysed in mineral acid such hydrochloric, sulphuric or phosphonic acid to provide the N-phosphonomethylamino acid (formula 1(b) wherein $R^{14}$ is H).

In a particularly preferred method methyl phosphonate or methyl phosphate ester compounds of the invention are prepared from a hexahydrazine of formula (VI):

(VI)

$$\begin{array}{c}\text{Z}\diagdown\text{A}\\ \big|\\ \text{N}\\ \diagup\quad\diagdown\\ \text{Z}\diagdown\text{A}\quad\text{N}\diagup\text{N}\diagdown\text{A}\diagup\text{Z}\end{array}$$

wherein Z is —C≡N or —C—$OOR^5$;
wherein $R^1$ is —C≡N or —$COOR^5$;
wherein $R^5$ is as hereinbefore defined but is typically other than hydrogen and
preferably is $C_1$ to $C_6$ alkyl or halogenated $C_1$ to $C_4$ alkyl.

The compounds of formula I wherein one of $R^2$ and $R^3$ is:

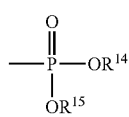

may be prepared by reaction of the hexahydrazine of formula VI with a phosphite of formula

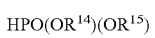

to provide the product of formula:

VII

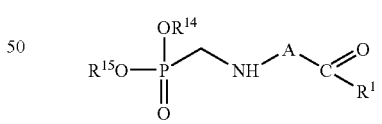

The acid of formula

VIII $$\text{HO}-\underset{\underset{\text{O}}{\|}}{\overset{\overset{\text{OH}}{|}}{\text{P}}}-\text{CH}_2-\text{NH}-\text{A}-\overset{\text{O}}{\underset{\text{OH}}{\|}}\text{C}$$

may be prepared by hydrolyses of the compound of formula VII for example in a mineral acid.

The hexahydrotriazene may be prepared by reaction of the protected amino acid of formula

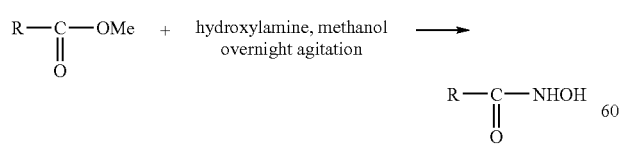

preferably as the hydrochloride salt with formaldehyde.

A preferred full scheme for this embodiment may be represented in Scheme 3 below:

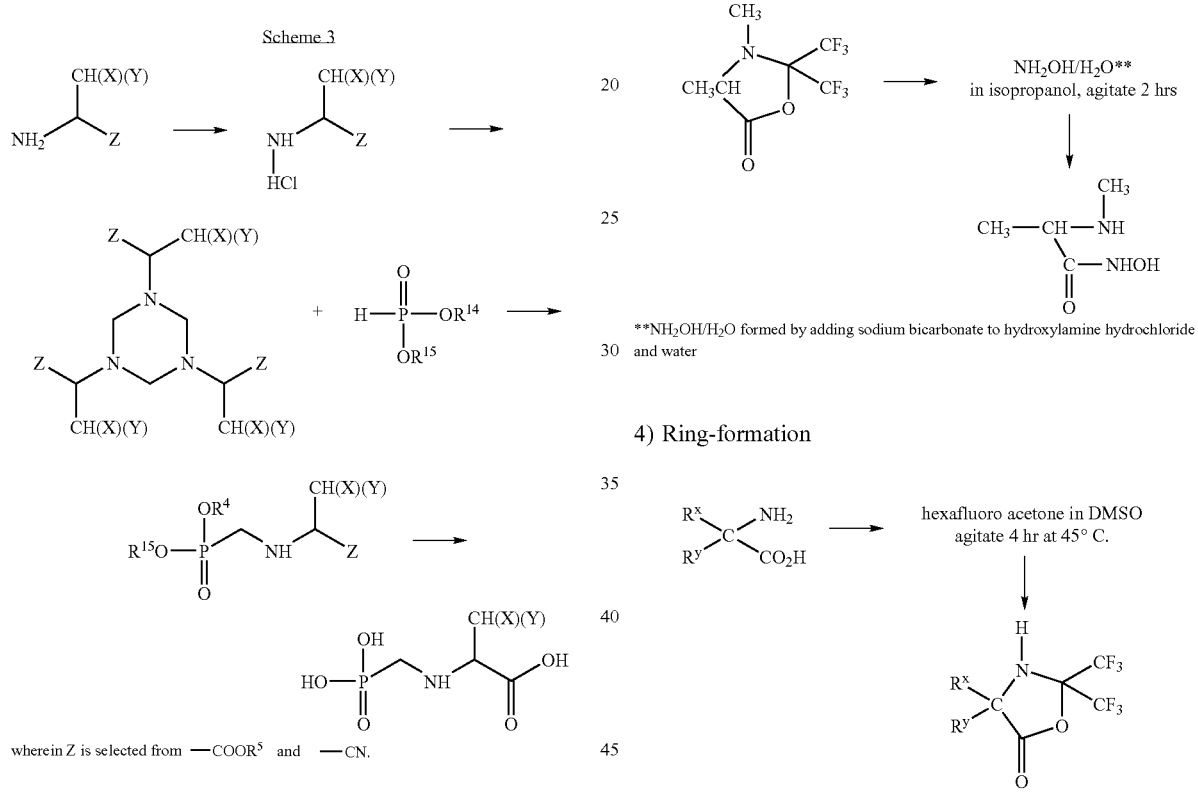

wherein Z is selected from —COOR$^5$ and —CN.

Further reactions which may be used to prepare the compounds of Table 1 and similar compounds including the following:

1) Preparation of hydroxamic acid derivatives may be prepared from acid derivatives such as lower alkyl esters by reaction with hydroxylamine R—C(=O)—OMe + hydroxylamine, methanol overnight agitation ⟶ R—C(=O)—NHOH 2) Generation of a phosphonic acid from phosphonic acid dialkyl ester such as the dimethyl ester may be carried out by reaction with trialkyl silyl bromide in a solvent such as acetonitrile

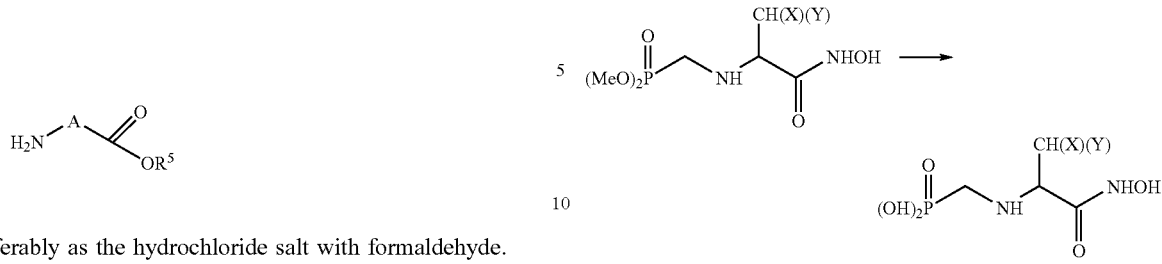

3) Ring-opening

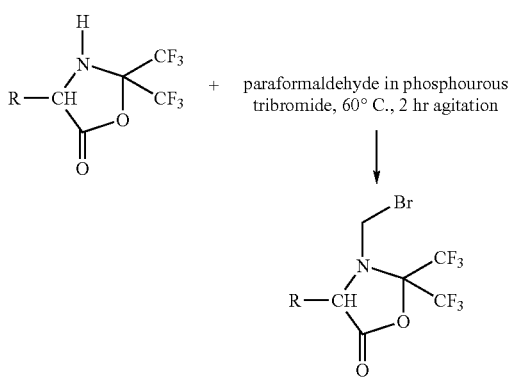

**NH$_2$OH/H$_2$O formed by adding sodium bicarbonate to hydroxylamine hydrochloride and water 4) Ring-formation R$^x$R$^y$C(NH$_2$)CO$_2$H + hexafluoro acetone in DMSO agitate 4 hr at 45° C. ⟶ oxazolidinone product 5) Bromomethylation oxazolidinone + paraformaldehyde in phosphourous tribromide, 60° C., 2 hr agitation ⟶ N-bromomethyl oxazolidinone 6) De-bromination

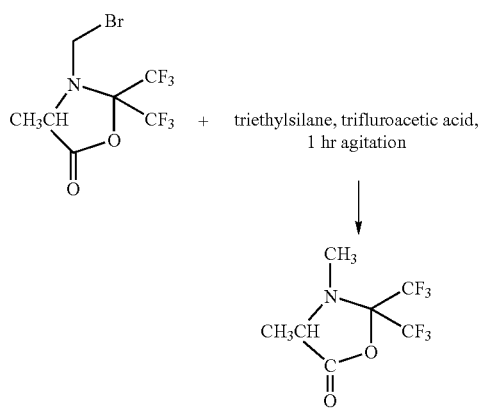

In one aspect the invention provides a method for the preparation of an insecticide of formula III

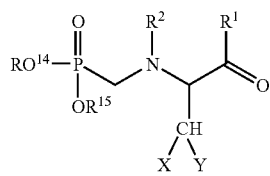

comprising reacting an amino acid or derivative thereof of formula (V)

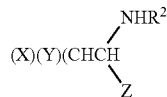

wherein Z is —CN or COOR$^5$ wherein R$^5$ is selected from the group consisting of alkyl, substituted alkyl, aryl, substituted aryl, cycloalkyl, substituted cycloalkyl, heterocyclic and substituted heterocyclic;

with a compound for formula

wherein R$^{12}$ and R$^{13}$ are independently selected from hydrogen, halogen, alkyl and haloalkyl;

reacting the intermediate with a phosphite of formula HPO(OR$^{14}$)(OR$^{15}$) wherein R$^{14}$ and R$^{15}$ are independently selected from the group consisting of alkyl, to provide the compound of formula III and optionally hydrolysing the ester groups to provide a compound of formula III wherein R$^{14}$ and R$^{15}$ are hydrogen and R$^1$ is hydroxy.

Preferred salts of compounds of formula I are salts formed with cations selected from the group consisting of alkali metals, alkaline earth metals, copper, zinc, manganese, nickel, ammonium, organic ammonium, organic sulphonium, and mixtures thereof. The most preferred salts are those in which at least one of the groups R$^5$, R$^{14}$ and R$^{15}$ is a counter ion and the others are hydrogen.

Examples of organic ammonium may be selected from the group consisting of monoalkylammonium, dialkylammonium, trialkylammonium, monoalkenylammonium, dialkenylammonium, trialkenylammonium, monoalkanolammonium, dialkanolammonium, trialkenolammonium, heterocylicammonium and aryl-ammonium. The preferred alkyl and alkenyl groups contain one to four carbon atoms.

The preferred salts are selected from the group consisting of alkali metals, alkaline earth metals, ammonium, alkyl ammonium (particularly isopropyl ammonium), trimesium and mixtures thereof.

Specific examples of the preferred compounds of the invention include: sodium salt of N-phosphonomethylvaline, ammonium salt of N-phosphonomethylvaline, isopropylammonium salt of N-phosphonomethylvaline, trimesium salt of N-phosphonomethylvaline, N-phosphonomethylleucine, sodium salt of N-phosphonomethylleucine, ammonium salt of N-phosphonomethylleucine, trimesium salt of N-phosphomethylleucine.

The compounds of Formula Ia, III and IV include at least one chiral centre at the α carbon atom (ie the carbon atom a to the carboxyl or carboxylate group). The compounds of the invention may be in the form of the L-enantiomer the D-enantiomer or racemic mixtures thereof. In one embodiment the compound of Formula I is comprised of at least 80% of one enantiomer and preferably at least 90% of one enantiomer.

The compounds of the invention preferably have stereochemistry of formula I(c):

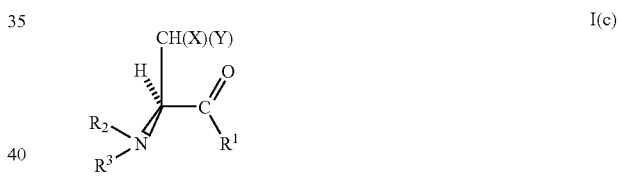

I(c)

The insecticide of the invention will preferably include at least 60% of the compounds of formula I(a) having stereochemistry of formula I(c) and more preferably at least 80% and most preferably at least 90%.

Compositions may be prepared in a stereo selective manner from the naturally occurring L-series amino acids. Preferably the compound of the invention is prepared from an amino acid composition comprising at least 80% more preferably at least 90% by weight of the amino acids (on a molar basis) in L-form.

In a further embodiment the invention provides an insecticidal composition comprising one or more compounds of Formula I and an agriculturally acceptable carrier.

The insecticidally effective carrier may be any of the carriers known in the art and may provide a solid granular product, an aqueous solution or an emulsion containing the active component.

The compounds of formula I may be applied directly to insects or the locus of insects such as plants to be protected or soil.

The compounds of formula I may be used on their own to kill insects, inhibit the growth of insects or reduce the damage caused by insects but are preferably used in the form of a composition comprising a compound of the invention in admixture with a carrier comprising a solid or liquid diluent.

Therefore, in yet a further aspect the invention provides an insecticidal compound as hereinbefore defined and carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifying concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example by coating or impregnating the preformed granular solid carrier with the active ingredient or by agglomeration techniques.

Examples of solid carriers include mineral earths and clays such as, for example, kaolin, bentonite, kieselguhr, Fuller's earth, Attaclay, diatomaceous earth, hole, loess, talc, chalk, dolomite, limestone, lime, calcium carbonate, powdered magnesia, magnesium oxide, magnesium sulfate, gypsum, calcium sulfate, prophyllite, silicic acid, silicates and silica gels; fertilizers such as, for example, ammonium sulfate, ammonium phosphate, ammonium nitrate and urea, natural products of vegetable origin such as, for example, grain means and flours, bark meals, wood meals, nutshell meals and cellulosic powders; and synthetic polymeric materials such as, for example, ground or powdered plastics and resins.

Alternatively, the solid compositions may be in the form of water soluble or water dispersible dusts, powders, granules or grains wherein the active ingredient and the solid carrier are combined with one or more surface active agents which act as wetting, emulsifying and/or dispersing agents to facilitate the dispersion or solubilisation of the active ingredient in liquid.

Examples of surface active agents include those of the cationic, anionic and non-ionic type. Cationic surface active agents include quaternary ammonium compounds, for example, the long chain alkylammonium salts, such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, and di- and tri-isopropylnaphthalenesulfonic acids, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the monoesters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenyl, octylphenol and nonylphenol; the condensation products of ethylene oxide with castor oil; alkyl polyglycoside surfactants; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and lecithins.

The liquid compositions may comprise a solution or dispersion of the active ingredient in a liquid carrier optionally containing one or more surface active agents which act as wetting, emulsifying and/or dispersing agents. Examples of liquid carriers include: water, mineral oil fractions such as, for example, kerosene, solvent naphtha, petroleum, coal tar oils and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfonoxide, N-methylpyrrolidone and sulfolane.

A preferred liquid composition comprises an aqueous suspension, dispersion or emulsion of the active ingredient which is suitable for application by spraying, atomising or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage to be capable of dilution with water to form aqueous preparations which remain homogenous for a sufficient time to enable them to be applied by conventional spray equipment. The concentrates conveniently contain from 20 to 80%, preferably 20 to 60% by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montomorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

Preferred solid compositions use water dispersible granule formulations comprising the active ingredient together with a solid carrier, optionally containing one or more solid or liquid surfactant active agents and other herbicidal adjuvants known to the art. The water dispersible granules may be prepared using methods known to the art, such as the wet granulation method.

The mode of application of the compositions of the invention will depend to a large extent on the type of composition used and the equipment available for its application. Solid compositions may be applied by dusting or any other suitable means for broadcasting or spreading the solid. Liquid compositions may be applied by spraying, atomising, watering, introduction into the irrigation water, or any other suitable means for broadcasting or spreading the liquid.

The compounds of the invention may be used in admixture with other insecticides to provide improved efficacy or more effective plant protection.

We have found that in combination with other insecticides provides a significant enhancement in activity which can be used to increase potency or to reduce the amount of other insecticide which is required to achieve pest control. While a wide range of known insecticides may be used in combination with the insecticide of the invention the composition of the invention preferably includes one or more insecticides selected from the group consisting of:

Organophosphorus compounds preferably selected from triazophos, monocrotophos, methamidophos, chlorpyrifos, parathion, acephate, profenofos, malathion, heptenophos;

Pyrethroids preferably selected from cypermethrin, cyhalothrin, lambdacyhalothrin, deltamethrin, fenvalerates, (alpha)-cypermethrin, cyfluthrin, fenpropathrin, etofenprox;

Carbamates preferably selected from aldicarb, bendiocarb, carbaryl, carbofuran, formetanates, pirimiocarb;

Biopesticides preferably selected from *bacillus thuringiensis*, granuloses and nuclear polyhedrosis viruses, *Beauveria bassiana, Beauveria brogniartii*, baculoviruses, such as *Autographa California*, Spinosad;

Others selected from endosulfan, abamectin, XDE-105, diafenthiuron, fipronil, chlorfenapyr, tebufenocides, fenazaquin, imidaclopride, triazamates, fentin, amitraz, MK-242; and 4-Haloalkyl-3 heterocyclylpyridines and 4-haloalkyl-5-heterocyclylpyrimidines and their salts.

The insecticidal composition of the invention preferably includes compositions of the insecticide of formula I together with another insecticide wherein the weight ratio is in the range of from 95:5 to 5:95 and more preferably from 9:1 to 1:9.

We have found that the activity of the insecticide of the invention may be significantly enhanced when it is used in combination with a chelating agent for divalent metals. Examples of chelating agents for divalent metals. Examples of chelating agents for divalent metals include compounds comprising a plurality of groups selected from carboxylic acid, carboxylate salt, hydroxyl amino, phosphoric acid, phosphonate salt.

Examples of preferred groups of chelating agents include amino polycaboxylic acid chelating agents, aromatic and aliphatic carboxylic acid chelating agents, amino acid chelating agents, ether polycarboxylic acid chelating agents, phosphonic acid chelating agents, hydroxycarboxylic acid chelating agents and dimethylglyoxime. The chelating agents may be in the form of the acid or salt particularly the sodium, potassium or ammonium salt.

Examples of aminopolycarboxylic chelating acids include ethylenediaminetetraacetic acid (EDTA), cyclohexanediaminetetraacetic acid (CDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH) and glycoletherdiaminetetracetic acid (GEDTA) ethylenediaminedisuccinic acid (EDDS) and salts thereof.

Examples of the aromatic or aliphatic carboxylic acid chelating agents to be used in the present invention include oxalic acid, succinic acid, pyruvic acid, salicylic acid and anthranilic acid, and salts, methyl esters and ethyl esters thereof. Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include compounds represented by the following formula, compounds similar to the compounds represented by the following formula and salts (e.g., sodium salt) thereof:

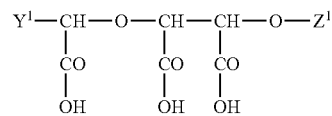

wherein $Y^1$ represents a hydrogen atom, a group represented by the formula: —$CH_2COOH$ or a group represented by the formula: —COOH, and $Z^1$ represents a hydrogen atom, a group represented by the formula: —$CH_2COOH$ or a group represented by the formula

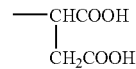

Examples of the hydroxy carboxylic acid chelating agents to be used in the present invention include malic acid, citric acid, glycolic acid, gluconic acid, heptonic acid, tartaric acid, lactic acid and salts thereof.

Examples of the electrolyte chelating agents of polymer (including oligomer) type to be used in the present invention include acrylic acid polymers, maleic anhydride polymers, α-hydroxyacrylic acid polymers, itaconic acid polymers, copolymers comprising at least two of the constituting monomers of these polymers and epoxysuccinic acid polymers.

In addition, chelating agents to be used in the present invention further include ascorbic acid and thioglycollic acid, and salts thereof.

The most preferred chelating agents are amino polycarboxylic acids, aliphatic carboxylic acids and hydroxycarboxylic acids and the most preferred chelating agent is EDTA which may be used in the form of the sodium salt such as the tetrasodium salt or the other suitable salt particularly water soluble salts.

The invention further provides a method of controlling insects comprising applying to the insects or the locus of the insects an effective amount of the compound of Formula I.

The compounds of the invention are particularly effective in controlling insects in crops. Examples of pests on which the insecticide of the invention may be effective include: insect species of the orders Lepidoptera, Hemiptera, Orthoptera, Coleoptera, Psocoptera, Isoptera, Thysanoptera and Homoptera. These pests which cause massive losses to many horticultural and broadacre crops and stored and manufactured grain products. Other examples of insect pests which may be controlled may include Diptera, Anaplura, Malophaga and Siponaptera cause parasitic infections in animals and man and Hymenoptera, Dictyoptera, Isoptera which are domestic and industrial pests.

Accordingly in a preferred embodiment of the method of the invention we provide a method of plant protection comprising applying to the plants an insecticidal composition as hereinbefore described.

The insecticides of the invention are particularly effective in controlling *Helicoverpa* spp (Heliothis, cotton budworm) in cotton.

The invention will now be described with reference to the following examples. It is to be understood that the examples are provided by way of illustration of the invention and that they are in no way limiting to the scope of the invention.

EXAMPLE 1

Preparation of N-Phosphonomethyl-L-Valine

N-Phosphonomethyl-L-Valine (see compound designated C1 in table below) is believed to be a new composition of matter, and was prepared according to Scheme 2 below.

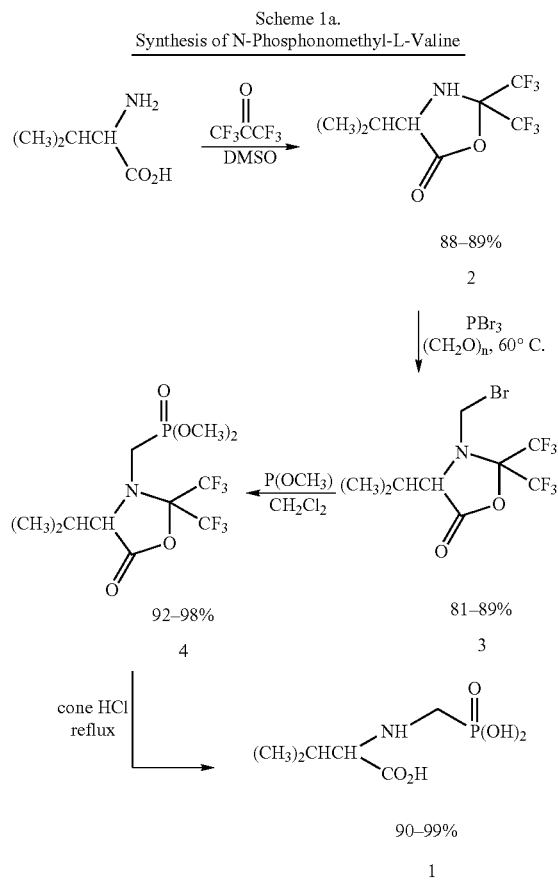

Other amino acids may be used in a similar way to valine in the above scheme.

The specific details of reaction in the synthesis of D(+) N-Phosphonomethyl-L-Valine were as follows (see also general reaction scheme which is provided above).

(a) Valine Plus Hexafluoroacetone

Hexafluoroacetone (10 g) was bubbled into a suspension of (L)-Valine (4.0 g, 34.1 mmol) in DMSO (30 mL) in a 2-necked round-bottomed flask equipped with a dry-ice condensor. Slight warming was necessary to prevent the DMSO from freezing. After a clear solution was obtained, excess hexafluoroacetone (2 g) was bubbled into the reaction mixture, and stirring continued for 3–4 h at ~45° C. (oil-bath temp). The excess hexafluoroacetone was distilled off into a water trap. The reaction mixture was poured into water (100 mL) and extracted with $CH_2Cl_2$ (2×50 mL). The combined organic extracts were washed with water (2×50 mL) and dried over anhydrous $Na_2SO_4$. The mixture was distilled at atmospheric pressure to remove the $CH_2Cl_2$.

Yield: 8.02 g (89%)—clear colourless liquid.

(b) Bromination

A mixture of valine trifluoromethyl oxazolidinone (8.0 g, 30 mmol), paraformaldehyde (1.81 g) and phosphorus tribromide (6 mL) was heated at 60° C. (oil-bath temp) for 2 h.

The reaction mixture was distilled under vacuum (≈0.1 mmHg)

Fraction 1, 25–30° C.—$PBr_3$

Fraction 2, 40–50° C.—clear colorless liquid, 9.6 g (89%)

(c) Phosphonate Ester Moiety

Trimethylphosphite (1.19 mL, 10 mmol, 1.2 equiv) was added dropwise to a solution of valine-methylbromide (3.0 g, 8.3 mmol, 1 equiv) and $CH_2Cl_2$ (5 mL) at room temp. Stirring was continued for 1 h. The reaction mixture was concentrated in vacuo, white solid, 3 g (92%).

(d) Hydrolysis of Phosphonate Ester

A soln of the valine-methylphosphonate (2.0 g, 5 mmol) and concentrated HCl (6 mL) was heated at reflux for 5 h. The reaction mixture was concentrated in vacuo. The residue was dissolved in ethanol. Propylene oxide (2 mL) was then added. A white solid precipitated. Ether (25 mL) was then added, and stirring continued for 15 min. The solid product was isolated by suction filtration, washed with ether and dried in vacuo. Yield 1.02 g (93%)—white solid (semi-solid at room temp).

(e) The L(−) isomer of N-phosphonomethylvaline may be prepared in the same manner as described above by using the D(+) enantiomer of valine.

(f) Optical Activity of N-phosphonomethylvaline

Relative optical rotation has been measured for the proposed L- and D-isomers of N-phosphonomethylvaline as well as their racemic mixture.

The optical rotation study was carried out on a ca. 0.25 M solutions of the above samples in the solvent comprised of distilled water (98% v/v), $KH_2PO_4$ (1.68 g/L), methanol (2.0% v/v) and 88% $H_3PO_4$ (0.2%). The following results were obtained.

1. The sample which was prepared from L-Valine (starting material) showed relative optical rotation ($[\alpha]_D$) to be +7.7°. This was calculated according to the following relationship $[\alpha]_D = (100 \times \alpha / (1 \times C)$
    where $\alpha$ is the measured angle (°) (0.8°)
    C is concentration of the sample (g/100 ml)(5.2 g/100 ml)
    l is length of observation tube (dm) (2 dm)
2. The sample which was prepared from D-Valine (starting material) showed relative optical rotation ($[\alpha]_D$) to be −12.5°.
    where $\alpha$ is the measured angle (°) (−1.2°)
    C is concentration of the sample (g/100 ml)(4.8 g/100 ml)
    l is length of observation tube (dm) (2 dm)
3. The sample which was prepared from DL-Valine (racemic) (starting material) showed relative optical rotation ($[\alpha]_D$) to be 0° (as expected).

EXAMPLES 2 TO 17

The compounds of examples 2 to 17 were prepared by a method in accordance with Example 1 and in accordance with information provided for the compounds in Table 1. The reagents were modified in accordance with the general procedure of scheme 1. Compounds 1 to 17 were subjected to bioassay in accordance with the following procedure and the results are shown in Table 2.

*Helicoverpa* Colony Maintenance

*H. armigera* were obtained from the CSIRO Entomology, Indooroopilly, QLD, Australia. *H. armigera* and *H. punctigera* were housed in independent constant temperature rooms (25–27 šC) with a 16/8 hour light/dark cycle. Larvae were reared in individual cups containing 1.5 cm cubes of media. Media comprised 234 g Haricot beans, 14 g agar, 35 g Tortula yeast, 50 g wheatgerm, 3.5 g ascorbic acid, 1.1 g sorbic acid and 2.2 g p-hydroxybenzoic methylester made up to 1 L with dH$_2$O, and was supplemented with 200 mg penicillin, 200 mg streptomycin and 16mg prochloraz. For every third generation of larvae raised, 50 mg chloramphenicol was added to 1 L of media. Care was taken during the rearing process to limit to potential for the development of contamination. To maintain viability, new larvae obtained from the field were added to the colony every third to fourth generation.

Media Bioassay

This assay was performed to investigate the efficacy of compounds in inhibiting larval growth. Media was prepared in an identical manner to that described above, and 5ml was added to wells containing 500 μl of test compound. Each compound was tested at 1.25, 2.5, 5 and 10 mM final concentration. The inhibitor was mixed evenly through the media, then the mixture was allowed to set. The media containing inhibitor was then divided between five plastic cups and two neonatal larvae were placed on the media in each cup. Larvae were left undisturbed for five days at 25–27 šC in a room with a 16/8 hour light/dark cycle. Controls, containing the solvent dimethyl sulfonoxide (DMSO) which was used for dissolving the inhibitor, were included in each assay. After 5 days all cups were transferred to –20 šC and left overnight before removal and weighing of the larvae. Larval weights were compared between treated and control groups. The results were expressed as a % inhibition, I, calculated as follows: I=100(1−A), where A is given by [(weight of control larvae) minus (weight of treated larvae)] divided by (weight of control larvae).

TABLE 2

| Ex. | Simple Name | % inhibition, I | Systematic Name |
|---|---|---|---|
| C1 | N-phosphonom ethyl valine | 62.5 | 3-Methyl-2-(phosphonom ethyl-amino)-butyric acid |
| C2 | leucine methylphosphonate hydroxamic acid | 59.7 | [(1-Hydroxycarbamoyl-3-methyl-butylamino)-methyl]-phosphonic acid monomethyl ester |
| C3 | phenylalanine-N-methyl phosphonyl hydroxamic acid | 49.9 | [(1-Hydroxycarbamoyl-2-phenyl-ethylamino)-methyl]-phosphonic acid monomethyl ester |
| C4 | N-methylalanine | 49.1 | 2-Methylamino-propionic acid |
| C5 | phenylalanine-N methyl phosphonic acid | 45.0 | 3-Phenyl-2-(phosphonom ethyl-amino)-propionic acid |
| C6 | N-methylalanine hydroxamic acid | 43.9 | N-Hydroxy-2-methylamino-propionamide |
| C7 | alanine hydroxamic acid-N methylphosphonate half methyl ester | 41.6 | [(1-Hydroxycarbamoyl-ethylamino)-methyl]-phosphonic acid monomethyl ester |
| C8 | leucine intermediate | 35.2 | 4-(2-methylpropyl)-3-(dimethoxy-phosphonomethyl)-2,2-bis-trifluoromethyl-oxazolidin-5-one |
| C9 | N-acetyl phenylalanine hydroxamic acid | 34.7 | 2-Acetylamino-N-hydroxy-3-phenyl-propionamide |
| C10 | threonine methyl phosphonate derivative | 34.4 | 2-[(Dimethoxy-phosphorylmethyl)-amino]-3-hydroxy-butyric acid methyl ester |
| C11 | phenylalanine methyl phosphonic acid intermediate | 29.2 | 4-Benzyl-3-bromomethyl-2,2-bis-trifluoromethyl-oxazolidin-5-one |
| C12 | valine N,N di-methyl phosphonate derivative | 28.0 | 2-[Bis-(dimethoxy-phosphorylmethyl)-amino]-3-methyl-butyric acid methyl ester |
| C13 | phenylalanine hydroxamate intermediate | 26.7 | 4-Benzyl-3-methyl-2,2-bis-trifluoromethyl-oxazolidin-5-one |
| C14 | valine N-methyl phosphonate hydroxamic acid | 24.4 | [(1-Hydroxycarbamoyl-2-methyl-propylamino)-methyl]-phosphonic acid |
| C15 | N-methylisoleucine | 24.4 | 3-Methyl-2-methylamino-pentanoic acid |
| C16 | leucine methylphosphonic acid hydroxamate | 24.3 | [(1-Hydroxycarbamoyl-3-methyl-butylamino)-methyl]-phosphonic acid |
| C17 | valine derivative | 20.3 | 2-Amino-1-(2-benzyloxymethyl-pyrrolidin-1-yl)-3-methyl-butan-1-one |

EXAMPLE 18

N-Phosphonomethyl-L-valine may also be prepared from (L)-valine by Mannich reaction according to the method of Scheme 3 shown below. This method is particularly suitable for larger scale preparations.

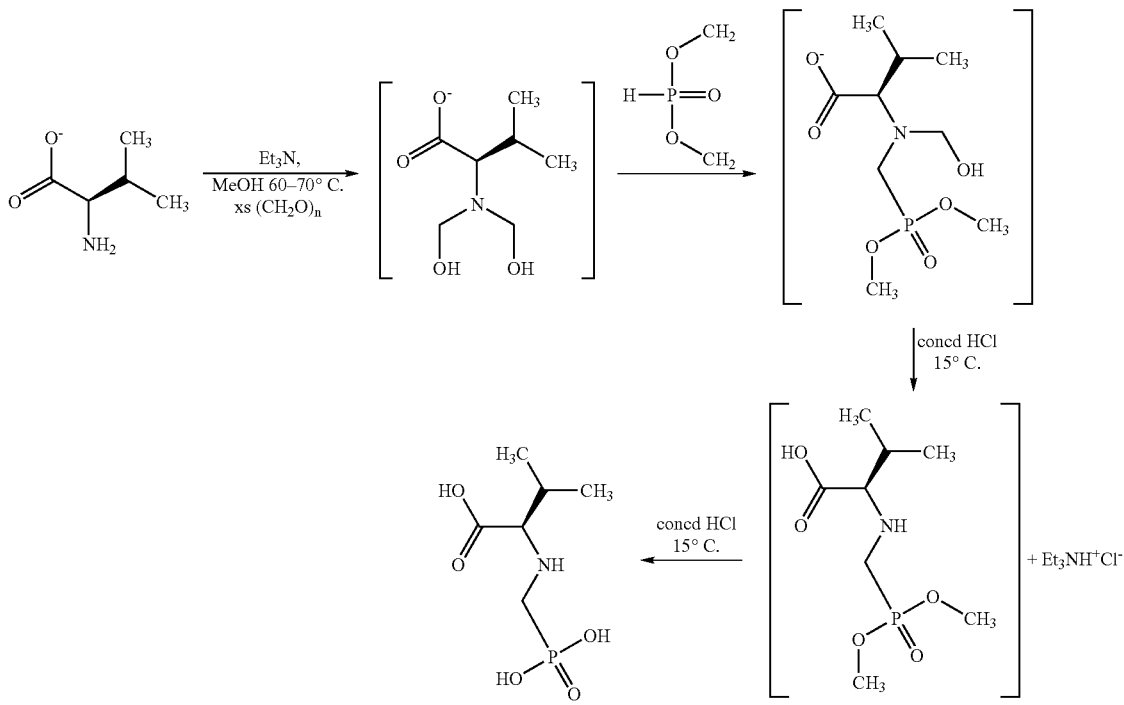

Scheme 3

EXAMPLE 19

Control of *Helicoverpa* spp. Larvae in a Commercial Cotton Crop

A field trial was conducted in a commercial cotton-growing region of Western Australia, as outlined below.

| Location: | Kununurra, Western Australia. |
|---|---|
| Dominant pest species: | *Helicoverpa armigera*: 186 (81%) of 230 third instar were *H. armigera* |
| Crop: | Cotton cv Delta Pine Emerald (broad leaf type). |
| Planting Details: | 7 to 8 plants per m of row, 2 rows 90 cm apart on beds at 1.8 m centres. |
| Plant Details: | About 1 metre tall at application. High foliage density; |
| Crop Stage: | Mid flowering. |
| Phytotoxicity at 7 days after application (DAA): | None. |

The trial was laid out as a randomized complete block experiment; with four blocks each containing one plot of each insecticidal treatment and one plot of the untreated control. Each block was comprised of consecutive plots 10 m long within the same strip of cotton. Buffer zones of several meters were left untreated between plots.

Treatments were:
C1@2.0 kg/ha
EDTA (previously been shown to have the ability to influence larval survival) @2.0 kg/ha and
C1 plus EDTA (1.0 kg/ha each).

No rain fell during the period of the trial, however dews formed before sunrise each day. Leaves were also coated with dust and ash from local bush fires. At 3 days after application (3DAA) total numbers of live viable *Helicoverpa* spp. larvae (TLVA) were counted on 10 terminals per plot.

Results were as follows.

TABLE 19.1

Influence of C1 and EDTA on the population of Helicoverpa spp.

| Treatment | | Mean number TLVA*/10 Terminals | |
|---|---|---|---|
| C1 (kg/ha) | EDTA (kg/ha) | −1 DAA | 3 DAA |
| 2 | 0 | 0.0 | 3.9 |
| 0 | 2 | 0.0 | 6.0 |
| 1 | 1 | 0.0 | 3.2 |
| 0 | 0 | 0.1 | 5.4 |

Although EDTA alone had no apparent influence on larval survival in this experiment (possibly because of washing by the dew or leaf contamination), C1 reduced the larval numbers by over 25% and the combined treatment of C1/EDTA at the same payload/ha reduced larval numbers by over 40%.

The trial showed that C1 plus EDTA was effective against *Helicoverpa* spp. infesting cotton and that mixing C1 and EDTA was more effective than using the components alone.

EXAMPLE 20

Insecticidal Activity of Racemic N-phosphonomethyl Valine (C1) Compared with its D an L Isomers The development of *helicoverpa* larvae on geranium plants was assessed in a glasshouse. Commercially grown geranium seedlings were potted (one plant/pot) two weeks prior to use. Seedlings used for experimental purposes were about 150 mm tall, with 4–7 leaves. On the day of treatment, plants were ranked by size and the ranking divided by the treatment number. Within these groupings plants were randomly allocated to a treatment grouping to provide 7 pots (plants) per treatment. Each group was isolated and sprayed with insecticidal treatments or water using a hand operated misting sprayer. Plants were then allowed to dry for approximately 1–2 hours before being placed in insect-proof cages in the glasshouse (one treatment/cage). Neonatal larvae of *H. armigera* were grown as outlined previously and 20 first instar larvae applied by evenly distributing them across all the leaves of each plant (generally 5 or 6 leaves) using a fine paint brush.

Assessments the total number of live, viable and active (TLVA) larvae, together with a subjective assessment of the percentage damage to leaves of each plant on days 3, 5 and 7 after application.

Two trials were conducted; one with just the isomeric variants of N-phosphonomethyl valine (C1) applied to the test plants and the second using two additives that had previously been found to improve the insecticidal activity of C1. These additives were EDTA (disodium, Sigma) and endosulfan (Endosulfan 350EC, Nufarm Ltd, 350 g/L endosulfan). In this trial EDTA was used at the same molar concentration as the racemic or isomeric C1. An appropriate sub-lethal concentration of endosulfan (suitable for use in glasshouse evaluations) was determined in previous dose-response evaluations. The suitable dose rate was $\frac{1}{250}^{th}$ of the rate recommended for use in the field (label rate, 2100 mL/Ha).

Isomeric versions of C1 were produced by the method outlined in Example 18, commencing with valine of known optical rotation properties.

The treatments are shown in Table 20.1.

TABLE 20.1

Products and dose rates used in evaluation of the isomeric forms C1.

| Code | Product and Dose |
|---|---|
| | Trial 1. |
| C1 | C1 manufactured from D,L-valine, designated 'racemic mixture' 25 mM dose |
| L-C1 | C1 manufactured using L-valine to provide the D(+) isomer 25 mM dose |
| D-C1 | C1 manufactured using D-valine, to provide the L(−) isomer 25 mM dose |
| UTC | Untreated Control (sprayed with dilution water) |
| | Trial 2. |
| C1 mix | C1 (25 mM) plus EDTA (25 mM) plus endosulfan ($\frac{1}{250}^{th}$ label rate) |
| L-C1 mix | L - C1 (25 mM) plus EDTA (25 mM) plus endosulfan ($\frac{1}{250}^{th}$ label rate) |
| D-C1 mix | D - C1 (25 mM) plus EDTA (25 mM) plus endosulfan ($\frac{1}{250}^{th}$ label rate) |
| UTC | Untreated Control (sprayed with dilution water) |

At −0.5, 3, 5 and 7DAA, numbers of *Helicoverpa armigera* larvae per leaf and per plant were counted, as well as a subjective (visual) assessment made of the percent leaf damage per plant.

Influence of the treatments on development of the population of *Helicoverpa* spp. and leaf damage produced by the larvae to 7 days after application (DAA) in the two trials are illustrated in Table 20.

TABLE 20.2

Insecticidal efficacy of racemic and isomeric forms of N-phosphonomethyl valine (C1) in glasshouse assessments.

| Treatment | Mean number of larvae/leaf at 7 DAA | Estimated leaf damage (%) at 7 DAA |
|---|---|---|
| | Trial 1 | |
| C1 | 2.8 | 43 |
| L-C1 | 2.3 | 35 |
| D-C1 | 3.5 | 55 |
| UTC | 3.6 | 63 |
| | Trial 2 | |
| C1 mix | 1.5 | 28 |
| L-C1 mix | 0.6 | 22 |
| D-C1 mix | 2.4 | 55 |
| UTC | 3.2 | 70 |

Insecticidal activity appeared to reside primarily with C1 manufactured using the L isomer of valine. This version of the compound remained compatible with EDTA and endosulfan.

EXAMPLE 21

Compatibility of C1/EDTA with other Insecticides (a) Endosulfan. Field Trial on Cotton.

Trial 2 in Example 20 indicated compatibility of endosulfan with a C1/EDTA mixture in the glasshouse. This was confirmed in a field trial on cotton conducted under the same conditions as those outlined for Example 19. This trial was however conducted later in the growing season with plants in the late flowering stage. Plants in this trial had clean leaves and neither rain nor dews were recorded over the trial period. Results are illustrated in Table 21.1.

TABLE 21.1

Compatibility of Endosulfan with a C1/EDTA mix in the field

| Treatment | | | |
|---|---|---|---|
| C1 plus EDTA (1 Kg/ha of each) | Endosulfan* (mL/ha) | TLVA*/10 terminals | |
| | | −0.5 DAA | Mean 3–7 DAA |
| − | 2100 | 1.6 | 1.9 |
| − | 210 | 1.5 | 4.1 |
| + | 210 | 1.6 | 1.6 |
| − | 0 | 1.3 | 3.9 |

*Endosulfan 350EC, Nufarm. Label (recommended field) rate for treatment of helicoverpa in cotton is 2.1 L/Ha.

Results confirmed compatibility of the C1/EDTA mix with endosulfan. Similar larval kill was obtained with C1/EDTA (1 Kg/Ha each) supplemented with endosulfan at $\frac{1}{10}^{th}$ label rate as was obtained with endosulfan at full label rate.

EXAMPLE 21 CONT

Compatibility of C1/EDTA with other Insecticides (b) Spinosad. Field Trial on Cotton A field trial was conducted in a commercial cotton-growing region of southern QLD (Dalby, Darling Downs). Pre-flowering cotton plants (7 to 8 plants/meter of row, two rows 90 cm apart on beds at 1.8 m centres. The trial was laid out as a complete block experiment; with four blocks each containing one plot of each insecticide treatment and one plot of the untreated control. Each block was six rows wide by 15 m long, with the central 4 m by 10 m sprayed. The treatments are tabulated below:

Products and dose rates used in the evaluation of the compatibility of spinosad with the C1/EDTA mixture were:
1. $C_1$ (1 Kg/Ha) plus EDTA (disodium (1 Kg/Ha).
2. Spinosad (Tracer, Dow Elanco, at label rate for treatment of *helicoverpa* in cotton; 150 mL/Ha)
3. Spinosad, 15 mL/Ha ($1/10^{th}$ label rate) C1 (1 Kg/Ha) plus EDTA (disodium (1 Kg/Ha) plus Tracer
4. (Spinosad) 15 mL/ha.
5. Untreated Control At −0.5, 3 and 8DAA, *Helicoverpa* spp. larvae, damaged squares and bolls were evaluated on a per meter of row basis. Rain (5 mm) fell during day 7 after treatment. Influence of the treatments on development of the population of *Helicoverpa* spp. over the trial period is illustrated in Table 21.2

TABLE 21.2

Population of *Helicoverpa* spp. over the trial period.

| Code | C1 kg/ha | EDTA Kg/Ha | Tracer mL/Ha | 0.5 DAA** | Mean number TLVA*/ meter of row 3 DAA | 8 DAA | Damaged squares and bolls/ meter of row 8 DAA |
|---|---|---|---|---|---|---|---|
| 1 | 0 | 0 | 0 | 2.25 b | 2.25 c | 4.63 b | 3.13 d |
| 2 | 1 | 1 | 0 | 1.50 ab | 0.88 b | 2.63 a | 1.50 c |
| 3 | 0 | 0 | 150 | 1.75 b | 0.38 a | 1.88 a | 0.75 a |
| 4 | 0 | 0 | 15 | 1.50 ab | 0.88 ab | 3.00 a | 1.38 bc |
| 5 | 1 | 1 | 15 | 1.50 ab | 0.75 ab | 2.00 a | 0.88 ab |
| | LSD 95% | | | 1.46 | 0.73 | 1.37 | 0.57 |

As in the previous examples, the reductions in larval numbers obtained when the individual components of mixed treatments were applied to cotton were too large to facilitate the demonstration of synergy. As demonstrated in the previous examples with endosulfan however, additive benefits were obtained by combining the C1/EDTA mixture with a spinosad. As with endosulfan, reductions in insect number were similar when the commercial insecticide was used at full label rate as when it was used at $1/10^{th}$ the recommended rate with the C1/EDTA mix.

EXAMPLE 21 CONT

Compatibility of C1/EDTA with other Insecticides (c) Chlorpyrifos. Field Trial on Peas.

A field trial was conducted as a single large plot trial in commercial pidgeon pea crop located in northern NSW (Dubbo). (7 to 8 plants/meter of row, six rows, 20 m long). Each sampling site consisted of one meter of row, well separated from surrounding treatments. Each treatment was randomly replicated four times across the plot. Insect populations were assessed by the 'beat sheet' method, as visual assessment of larvae in standing crops of this type is difficult. The beat sheet method of larval assessment consists of placing a white sheet under the section of crop to be assessed and the crop is vigorously shaken to dislodge larvae onto the sheet. The treatments are tabulated below:

1. C1 (1 Kg/Ha) plus EDTA (disodium (1 Kg/Ha).
2. Chlorpyrifos (Pirate 300 g/L EC, Nufarm, at label rate for treatment of helicoverpa in cotton; 4.0 L/ha)
3. Chlorpyrifos 0.4 L/ha ($1/10^{th}$ label rate)
4. C1 (1 Kg/Ha) plus EDTA (disodium (1 Kg/Ha) plus Pirate 0.4 L/ha.
5. Untreated Control Pre-treatment and at 2 and 5DM, the number and *Helicoverpa* spp. larvae were evaluated on a per meter of row basis.

Results

Influence of the treatments on development of the population of *Helicoverpa* spp. over the trial period is illustrated in Table 21.3.

TABLE 21.3

Insecticidal activity of chlorpyrifos combinations.

| Code | Mean number of small larvae/ metre of row at 5 DAA | Mean number of medium larvae/meter of row at 5 DAA | Mean number of large larvae/meter of row at 5 DAA | Mean total number of larvae/meter of row at 5 DAA |
|---|---|---|---|---|
| 1 | 0.3 | 5.0 | 6 | 11.3 |
| 2 | 0.0 | 2.3 | 3.8 | 6.0 |
| 3 | 1.5 | 6.0 | 4.8 | 12.3 |
| 4 | 0.0 | 2.5 | 3.8 | 6.3 |
| 5 | 1.5 | 7.8 | 5.8 | 15.0 |

The sum of the reductions in total larvae/meter of row obtained when the C1/EDTA component and the '$1/10^{th}$ rate' chlorpyrifos treatment were used alone was less than the larval reduction noted when the two treatments were used together. This indicates synergistic insect control by the combined treatment. The results of this trial were consistent with previous trials in the glasshouse, which indicated that medium and large larvae were little affected by exposure to the C1/EDTA mixture alone. The results of this trial demonstrate that medium and large larvae are well controlled by a C1/EDTA when combined with a low rate chlorpyrifos.

EXAMPLE 21 CONT

Compatibility of C1/EDTA with other Insecticides (d) Abamectin. Glasshouse Trial. *Helicoverpa Armicera* on Geranium Seedlings The potential of abamectin as a co-insecticide with a mixture of C1plus EDTA was assessed by exposing *Helicoverpa armigera* larvae to the mixture and its component parts in a glasshouse experiment. Geranium seedlings were prepared and treated as outlined in Example 20, except that the plants were sprayed with products outlined below.

1. Abamectin 18 g/L EC (Nufarm, trial formulation) applied at $1/250^{th}$ the recommended rate for field use (6 mL/L). A previous dose titration had indicated that this dilution was likely to give a sub-lethal response.
2. C1 (25 mM) plus abamectin ($1/250^{th}$ of 6 mL/L).

3. C1 (25 mM) plus EDTA (disodium, 25 mM) plus abamectin (1/250$^{th}$ of 6 mL/L).

4. Untreated Control

Assessments the total number of live, viable and active (TLVA) larvae, together with a subjective assessment of the percentage damage to leaves of each plant were made on days 3, 5 and 7 after application.

The number of *Helicoverpa armigera* larvae per leaf, as well as a subjective (visual) assessment of the percent leaf damage per plant was made on day 7 after application (7DAA).

Results

Influence of the treatments on survival of *H. armigera*. is illustrated in Table 21.4.

TABLE 21.4

Insecticidal activity of abamectin combinations.

| Code | Mean number of larvae/ leaf at 7 DAA | Estimated leaf damage (%) at 7 DAA |
|---|---|---|
| 1 | 0.1 | 17 |
| 2 | 0 | 9 |
| 3 | 0.1 | 7 |
| 4 | 2.8 | 59 |

The death rate of *helicoverpa* due to abamectin alone was higher than anticipated in this trial, however addition of C1 or C1 plus EDTA reduced leaf damage by the insects.

EXAMPLE 21 CONT

Compatibility of C1/EDTA with other Insecticides (e) Carbaryl. Glasshouse Trial. *Helicoverpa armigera* on Geranium Seedlings.

The potential of carbaryl as a co-insecticide with a mixture of C1 plus EDTA was assessed by exposing *Helicoverpa armigera* larvae to the mixture and its component parts in a glasshouse experiment. Geranium seedlings were prepared and treated as outlined in part d (above), except that the plants were sprayed with products outlined below.

1. Carbaryl (Arthur Yates Pty Ltd, 100 g/L EC) applied at 1/100$^{th}$ the recommended rate for field use (10 mL/L). A previous dose titration had indicated that this dilution was likely to give a sub-lethal response.

2. C1 (25 mM) plus EDTA (disodium, 25 mM).

3. C1 (25 mM) plus EDTA (25 mM) plus carbamate (0.1 mL/L).

4. Untreated Control.

Assessments the total number of live, viable and active (TLVA) larvae, together with a subjective assessment of the percentage damage to leaves of each plant was made on day 7 after application (7DAA).

Results

Influence of the treatments on development of the population of Helicoverpa spp. over the trial period is illustrated in Table 21.5.

TABLE 21.5

Insecticidal activity of carbaryl combinations.

| Code | Mean number of larvae/ leaf at 7 DAA | Estimated leaf damage (%) at 7 DAA |
|---|---|---|
| 1 | 1.20 | 41 |
| 2 | 1.45 | 41 |
| 3 | 0.60 | 23 |
| 4 | 2.25 | 65 |

The results indicate the insecticidal performance of a C1/EDTA mix can be improved by concurrent use of a low rate of carbaryl.

The invention claimed is:

1. An insecticide comprising at least one compound selected from the group consisting of compounds of formula I(a) and salts derived therefrom

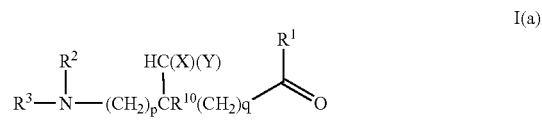

I(a)

wherein:
R$^1$ is selected from the group consisting of:
—OR$^5$ wherein R$^5$ is selected from the group consisting of hydrogen, alkyl, substituted alkyl, aryl, substituted aryl, cycloalkyl, substituted cycloalkyl, heterocyclic and substituted heterocyclic;
—NR$^6$OH wherein R$^6$ is selected from the group consisting of hydrogen, alkyl, substituted alkyl, aryl, substituted aryl, carbocyclic and substituted carbocyclic;
—NR$^7$R$^8$ wherein R$^7$ and R$^5$ are independently selected from the group consisting of hydrogen, alkyl, substituted alkyl, aryl, substituted aryl and carbocyclic; and
a group wherein R$^1$ is linked to R$^2$ to form a diradical bridging group;
R$^2$ is selected from the group consisting of hydrogen, alkyl, substituted alkyl, carbocyclic, substituted carbocyclic, aryl, substituted aryl, acyl and substituted acyl;
R$^3$ is selected from the group consisting of substituted alkyl, substituted haloalkyl, substituted acyl, substituted aryl, substituted alkylaryl and substituted arylalkyl, wherein the substituent is a group of the formula

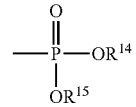

wherein R$^{14}$ and R$^{15}$ are independently selected from the group consisting of hydrogen, alkyl, aryl, aralkyl, alkylaryl, haloalkyl, haloaryl, haloakylaryl, and haloaralkyl;
R$^{10}$, X and Y are independently selected from the group consisting of hydrogen, alkyl, thiol, hydroxy, thioalkyl, alkoxy, substituted alkyl, carbocyclic, substituted carboxyclic, heterocyclic and substituted heterocyclic; and
p and q are independently selected from 0, 1, 2 and 3.

2. An insecticide according to claim 1 comprising at least one compound selected from the group consisting of compounds of formula III and salts derived therefrom $$RO^{14}-\underset{\underset{OR^{15}}{\|}}{\overset{O}{P}}-CH_2-\underset{\underset{\underset{X\ Y}{CH}}{|}}{N}-\underset{R^2}{\overset{R^1}{C}}=O$$
III 3. An insecticide according to claim 2 wherein
R$^1$ is selected from the group consisting of:
- —OR$^5$ wherein R$^5$ is selected from the group consisting of hydrogen, alkyl, haloalkyl, aryl substituted alkyl, heterocyclic, heterocyclic substituted with alkyl wherein the alkyl is optionally further substituted with hydrocarbyloxy;
- —NR$^6$OH wherein R$^6$ is selected from the group consisting of hydrogen, alkyl, substituted alkyl, aryl, substituted aryl, carbocyclic and substituted carbocyclic;
- —NR$^7$R$^8$ wherein R$^7$ and R$^8$ are independently selected from hydrogen and C$_1$ to C$_6$ alkyl; and
- a group wherein R$^1$ is linked to R$^2$ to form a bridging group —R$^2$—R$^1$— of formula —(CR$^{12}$R$^{13}$)$_n$O$_q$—;

wherein n is 1 or 2, q is zero or 1 and R$^{12}$ and R$^{13}$ are independently selected from hydrogen, halogen, alkyl and haloalkyl;
R$^2$ is selected from the group consisting of:
hydrogen, alkyl, haloalkyl, aryl, alkylaryl and aralkyl; substituted alkyl, substituted haloalkyl, substituted acyl, substituted aryl,
substituted alkylaryl and substituted arylalkyl, wherein the substituent is a group of formula $$-\underset{\underset{OR^{15}}{|}}{\overset{\overset{O}{\|}}{P}}-OR^{14}$$

wherein R$^{14}$ and R$^{15}$ are independently selected from the group consisting of hydrogen, halo, alkyl, aryl, alkanoyl, alkylaryl, aralkyl, haloalkyl, haloaryl, haloalkyl aryl and haloarylalkyl;
a group wherein R$^2$ is linked to R$^1$ to provide the group —R$^2$—R$^1$— of formula —(CR$^{12}$R$^{13}$)$_n$O$_p$— wherein n is 1 or 2, p is 0 or 1 and R$^{12}$ and R$^{13}$ are independently selected from hydrogen, alkyl and haloalkyl;
p and q are independently selected from 0 and 1; and
X and Y are independently selected from the group consisting of hydrogen, C$_1$ to C$_6$ alkyl, thiol, hydroxy, C$_1$ to C$_6$ thioalkyl, C$_1$ to C$_6$ alkoxy, substituted C$_1$ to C$_6$ alkyl, C$_4$ to C$_6$ carboxylic substituted C$_4$ to C$_6$ heterocyclic and substituted C$_4$ to C$_6$ heterocyclic.

4. An insecticide according to claim 2 wherein
R$^1$ is selected from the group consisting of
hydroxy, C$_1$ to C$_6$ alkyl, halogenated C$_1$ to C$_4$ alkyl;
—NR$^6$OH wherein R$^6$ is selected from the group consisting of hydrogen, alkyl, substituted alkyl, aryl, substituted aryl, carbocyclic and substituted carbocyclic;
—NR$^7$R$^8$ wherein R$^7$ and R$^8$ are independently selected from hydrogen and C$_1$ to C$_4$ alkyl;
R$^2$ is selected from the group consisting of
hydrogen C$_1$ to C$_8$ alkyl, halogen-substituted C$_1$ to C$_6$ alkyl, and C$_1$ to C$_6$ alkyl substituted by a group of the formula $$-\underset{\underset{OR^{15}}{|}}{\overset{\overset{O}{\|}}{P}}-OR^{14}$$

wherein R$^{14}$ and R$^{15}$ are independently selected from the group consisting of hydrogen and C$_1$ to C$_4$ alkyl; and
X and Y are independently selected from the group consisting of hydrogen, C$_1$ to C$_4$ alkyl thiol, aryl, hydroxyaryl, acyl, aryl substituted C$_1$ to C$_4$ alkyl, heterocyclic, thio-substituted C$_1$ to C$_4$ alkyl, amino-substituted C$_1$ to C$_4$ alkyl and hydroxyalkyl.

5. An insecticide according to claim 2 wherein the group HC(X)(Y) is selected from the group consisting of: —CH$_3$, —CH(CH$_3$)$_2$, —CH$_2$CH$_2$SCH$_3$, —CH$_2$CH(CH$_3$)$_2$, —CH$_2$CH$_2$CH$_2$NHCNHNH$_2$, —CH$_2$C$_6$H$_5$OH, —CH(CH$_3$)CH$_2$CH$_3$, —CH$_2$—C=C—H, —CH$_2$-(indole),
       |   |
       N   N
        \ /
         C
         |
         H —CH$_2$OH, —CH(OH)CH$_3$, —CH$_2$SH, —CH$_2$—(phenyl), —(CH$_2$)$_4$—NH$_2$ and —(CH$_2$)$_2$NH$_2$.

6. An insecticide according to claim 1 wherein said at least one compound comprises a compound of formula IV(a):

IV(a)

$$R^3-N\underset{}{\overset{R^{12}\ R^{13}}{\diagup}}\underset{X\ Y}{\diagdown}(O)p$$

wherein n is 1 or 2, p is 0 or 1, R$^{12}$ and R$^{13}$ are independently selected from hydrogen, alkyl and haloalkyl.

7. An insecticide according to claim 1 wherein said at least one compound comprises a compound of formula Ia Iae $$\underset{R^3}{\overset{R^2}{\diagdown}}N-\underset{\underset{R^1}{|}}{\overset{CH(X)(Y)}{C}}=O$$

and wherein at least 60 mole percent of said compound has the stereochemistry of formula I(c):

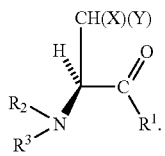

I(c)

8. An insecticide according to claim 7 wherein at least 80% of the compound Ic has the stereochemistry I(c).

9. An insecticide according to claim 7 wherein at least 90% of the compound Ic has the stereochemistry I(c).

10. An insecticide according to claim 2 wherein said at least one compound comprises is derived from an amino acid comprising at least 80% of the L-enantiomer.

11. An insecticide according to claim 1 comprising a compound selected from the group consisting of 3-Methyl-2-(phosphonomethyl-amino)-butyric acid; [(1-Hydroxycarbamoyl-3-methyl-butylamino)-methyl]-phosphonic acid monomethyl ester; [(1-Hydroxycarbamoyl-2-phenyl-ethylamino)-methyl]-phosphonic acid monomethyl ester; Phenyl-2-(phosphonomethyl-amino)-propionic acid; 4-(2-methylpropyl)-3-(dimethoxy-phosphonomethyl)-22-bis-trifluoromethyl-oxazolidin-5-one; 2-[(Dimethoxy-phosphorylmethyl)-amino]-3-hydroxy-butyric acid methyl ester; 2-[Bis-(dimethoxy-phosphorylmethyl)-amino]-3-methyl-butyric acid methyl ester; [(1-Hydroxycarbamoyl-2-methyl-propylamino)-methyl]-phosphonic acid; [(1-Hydroxycarbamoyl-3-methyl-butylamino)-methyl]-phosphonic acid and the salts thereof.

12. An insecticide according to claim 1 comprising N-phosphonomethyl valine and agriculturally acceptable salts thereof.

13. An insecticide according to claim 1 comprising one or more salts of N-phosphonomethyl valine selected from the group consisting of monoalkylammonium, dialkylammonium, trialkylammonium, monoalkenylammonium, dialkenylammonium, trialkenylammonium, monoalkanolammonium, dialkanolammonium, trialkanolammonium, heterocylicammonium and arylammoniun.

14. An insecticide according to claim 1 comprising N-phosphonomethyl valine wherein at least 80% of N-phosphonomethyl valine is the D(+) enantiomer.

15. An insecticide according to claim 2 further comprising a chelating agent for divalent metals.

16. An insecticide according to claim 15 wherein the chelating agent is selected from the group consisting of polycaboxylic acid chelating agents, aromatic and aliphatic carboxylic acid chelating agents, amino acid chelating agents, ether polycarboxylic acid chelating agents, phosphonic acid chelating agents, hydroxycarboxylic acid chelating agents and dimethylglyoxime, in their acid or salt forms.

17. An insecticide according to claim 1 further comprising at least one second insecticidal compound selected from the group consisting of organophosphorus compounds, pyrethoids, carbamates, biopesticides, endosulfan, abemectin, XDE-105, diafenthiuron, fipronil, chlorfenapyr, tebufenocides, fenazaquin, imidacloprid, triazamates, fentin amitraz, MK-242 and 4-haloalkyl-3-heterocyclylpyridines and 4-haloalkyl-5-heteroxyclyl-pyremides and their salts.

18. An insecticide according to claim 17 wherein said at least one second insecticidal compound comprises an insecticide selected from the group consisting of spinosad, endosulfan and amitraz.

19. An insecticide according to claim 17 wherein the weight ratio of the compound of formula I(a) to said second insecticidal compound is from 95:5 to 9:95.

20. An insecticide according to claim 1 wherein the insecticide comprises from 1 to 99% by weight of a compound of formula I(a) and an agriculturally acceptable carrier therefor.

21. An insecticide according to claim 20 wherein the insecticide includes an agriculturally acceptable carrier and a surface active agent.

22. A method of controlling insects comprising applying to a locus of insects an insecticide according to claim 1.

23. A method of controlling insects in crops comprising applying to the crop an effective amount of an insecticide according to claim 1.

24. A method according to claim 22 wherein the insecticide is used to control insect species selected from the orders Hepidoptera, Hemiptera, Orthoptera, Coleopteran, Psocoptera, Isoptera, Physaloptera and Homoptera.

25. A method according to claim 23 wherein the crop is cotton.

26. A method for the preparation of an insecticide of formula III

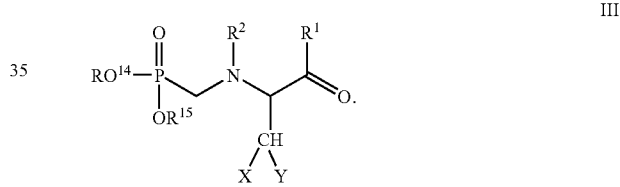

III wherein:

$R^1$ is selected from the group consisting of:
—$OR^5$ wherein $R^5$ is selected from the group consisting of hydrogen, alkyl, substituted alkyl, aryl, substituted aryl, cycloalkyl, substituted cycloalkyl, heterocyclic and substituted heterocyclic;
—$NR^6OH$ wherein $R^6$ is selected from the group consisting of hydrogen, alkyl, substituted alkyl, aryl, substituted aryl, carbocyclic and substituted carbocyclic;
—$NR^7R^8$ wherein $R^7$ and $R^5$ are independently selected from the group consisting of hydrogen, alkyl, substituted alkyl, aryl, substituted aryl and carbocyclic; and
a group wherein $R^1$ is linked to $R^2$ to form a diradical bridging group;

$R^2$ is selected from the group consisting of hydrogen, alkyl, substituted alkyl, carbocyclic, substituted carbocyclic, aryl, substituted alkyl, acyl and substituted acyl;

X and Y are independently selected from the group consisting of hydrogen, $C_1$ to $C_6$ alkyl, thiol, hydroxy, $C_1$ to $C_6$ thioalkyl, $C_1$ to $C_6$ alkoxy, substituted $C_1$ to $C_6$ alkyl, $C_4$ to $C_6$ carboxylic substituted $C_4$ to $C_6$ heterocyclic and substituted $C_4$ to $C_6$ heterocyclic;

said method comprising reacting an amino acid of formula (V) or derivative thereof

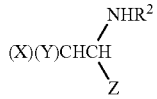 (V)

wherein Z is —CN or COOR⁵;
with a compound of the formula

wherein $R^{12}$ and $R^{13}$ are independently selected from hydrogen, halogen, alkyl and haloalkyl to form an intermediate;

reacting the intermediate with a phosphite of formula $HPO(OR^{14})(OR^{15})$ wherein $R^{14}$ and $R^{15}$ are independently selected from the group consisting of alkyl, to provide a compound of formula III; and optionally hydrolysing the ester groups to provide a compound of formula III wherein $R^{14}$ and $R^{15}$ are hydrogen and $R^1$ is hydroxy.

27. A compound selected from the group consisting of N-phosphonomethyl valine and salts thereof.

28. A compound according to claim 27 wherein at least 80% of the compound is in the form of the D(+) enantiomer.

* * * * *